(12) United States Patent
Jeon et al.

(10) Patent No.: US 9,513,254 B2
(45) Date of Patent: Dec. 6, 2016

(54) MICROFLUIDIC SENSOR PACKAGE STRUCTURE AND METHOD

(71) Applicant: Amkor Technology, Inc., Chandler, AZ (US)

(72) Inventors: Hyung Il Jeon, Gyeonggi-do (KR); Ji Young Chung, Gyeonggi-do (KR); Chan Ha Hwang, Gyeonggi-do (KR); Byong Jin Kim, Gyeonggi-do (KR); Yung Woo Lee, Gyeonggi-do (KR); Do Hyun Na, Seoul (KR); Jae Ung Lee, Seoul (KR)

(73) Assignee: Amkor Technology, Inc., Tempe, AZ (US)

( * ) Notice: Subject to any disclaimer, the term of this patent is extended or adjusted under 35 U.S.C. 154(b) by 93 days.

(21) Appl. No.: 14/455,975

(22) Filed: Aug. 11, 2014

(65) Prior Publication Data
US 2015/0041324 A1 Feb. 12, 2015

(30) Foreign Application Priority Data
Aug. 12, 2013 (KR) .................. 10-2013-0095147

(51) Int. Cl.
| | | |
|---|---|---|
| *B01L 3/00* | (2006.01) | |
| *G01N 33/487* | (2006.01) | |
| *H01L 23/433* | (2006.01) | |
| *G01N 27/447* | (2006.01) | |
| *H01L 23/34* | (2006.01) | |

(52) U.S. Cl.
CPC ... *G01N 27/44791* (2013.01); *B01L 3/502707* (2013.01); *G01N 33/48721* (2013.01); *B01L 3/50273* (2013.01); *B01L 3/502715* (2013.01); *B01L 3/502761* (2013.01); *B01L 2200/12* (2013.01); *B01L 2300/0645* (2013.01); *B01L 2300/0816* (2013.01); *B01L 2300/0858* (2013.01); *B01L 2400/0406* (2013.01); *B01L 2400/0415* (2013.01); *H01L 23/4334* (2013.01); *Y10T 29/4913* (2015.01)

(58) Field of Classification Search
CPC ............... B01L 2300/0645; B01L 2300/0816; B01L 2300/0858; B01L 2400/0406; B01L 2400/0415; B01L 3/502707; B01L 3/50273; B01L 3/502761; G01N 27/44791; G01N 33/48721; Y10T 29/4913
See application file for complete search history.

(56) References Cited

U.S. PATENT DOCUMENTS

| | | | |
|---|---|---|---|
| 6,455,927 B1 | 9/2002 | Glenn et al. | |
| 6,548,895 B1* | 4/2003 | Benavides | H01L 23/4334 137/594 |
| 2004/0189311 A1* | 9/2004 | Glezer | B01L 3/5027 324/444 |

(Continued)

OTHER PUBLICATIONS

Office Action received from Korean Patent Office in Korean; English Translation Not Available; Date: Sep. 1, 2014; 5 pages.

(Continued)

*Primary Examiner* — Jennifer Wecker
(74) *Attorney, Agent, or Firm* — Kevin B. Jackson

(57) ABSTRACT

In one embodiment, a microfluidic sensor device includes microfluidic sensor mounted on and electrically connected a micro lead frame substrate. The microfluidic sensor is molded to form a package body. The package body includes a molded panel portion and, in some embodiments, a mask portion having one or more open channels, sealed channels, and/or a sealed chamber exposing an active surface of the microfluidic sensor. The molded panel portions and mask portions are configured to allow a material to dynamically or statically contact the microfluidic sensor for analysis.

12 Claims, 7 Drawing Sheets

(56) References Cited

U.S. PATENT DOCUMENTS

2008/0311000 A1* 12/2008 Wimberger-Friedl B01L 3/502707
                                                          422/68.1
2011/0229375 A1   9/2011  Ehrenpfordt et al.
2012/0061239 A1*  3/2012  Elibol .............. B01L 3/502715
                                                          204/406
2013/0153933 A1*  6/2013  Lee ................... H01L 31/1876
                                                          257/82
2014/0227147 A1*  8/2014  Beyer ................ B81C 1/00119
                                                          422/502

OTHER PUBLICATIONS

Kuo et al., "MEMS Package Fabrication Method and Structure", U.S. Appl. No. 13/766,171, filed Feb. 13, 2013.

Kuo et al, "Microfluidic Sensor Package Fabrication Method and Structure", U.S. Appl. No. 13/793,541, filed Mar. 11, 2013.

No author provided, "Polymerase chain reaction", 12 pages, Retrieved on Jul. 24, 2014 from URL: <http://en.wikipedia.org/wiki/Polymerase_chain_reaction>.

* cited by examiner

MICROFLUIDIC SENSOR PACKAGE STRUCTURE AND METHOD

CROSS REFERENCE TO RELATED APPLICATION

This application claims priority to Korean Patent Application No. 10-2013-0095147 filed on Aug. 12, 2013, which is expressly incorporated by reference herein.

BACKGROUND

Embodiments disclosed herein relate generally to electronic devices and, more specifically, to microfluidic sensor package structures including one or more spaces for containing a material to be analyzed and methods of fabricating the same.

A microfluidic sensor is an electronic device configured to analyze various kinds of materials while requiring that only a small amount of material be used for the analysis. Microfluidic sensors have been used in separating and synthesizing various kinds of materials in addition to analyzing such materials.

In the past, microfluidic sensors have been fabricated to have a structure, such as a micrometer-sized channel or chamber, such that a material (for example, blood, a chemical material, or other biological material) can be placed proximate to the sensor portion of the device for analysis. Microfluidic sensors have been used in various fields, such as DNA examination, fundamental scientific research of chemical or biological materials, disease diagnosis, cell culture, and various chemical reactions as well as other fields.

For this purpose, microfluidic sensors have been provided with a channel for carrying a material to be analyzed as the material passes over the sensor chip for analysis, or with a chamber for containing and storing the material on the sensor chip for analysis. In previous microfluidic sensors, photolithographic techniques were used to form micrometer-sized metalized stand-offs, which defined channels or chambers, directly on the surface of a microfluidic sensor in wafer form during front-end wafer processing. This approach has had several problems including requiring expensive apparatuses be used, such as spin coaters for applying photoresist and ultraviolet aligners to expose the photoresist and pattern the metalized stand-offs. Also, photolithographic process control has been difficult for microfluidic sensors. Furthermore, this conventional technology has been problematic because the metalized stand-offs are formed directly on the surface of the microfluidic sensor during front-end wafer processing, and thus, the microfluidic sensors are susceptible to scratch damage and/or impact damage, which have decreased the reliability of the devices.

Finally, previous microfluidic sensors devices used expensive printed circuit board ("PCB") substrates for packaging the devices, which were expensive and added manufacturing costs.

Accordingly, it is desirable to have a microfluidic sensor structure and method that overcome the issues with previous microfluidic devices described previously, as well as others. It is also desirable to have a structure and method that is cost effective, easy to integrate into assembly process flows, and reliable.

For simplicity and clarity of the illustration, elements in the figures are not necessarily drawn to scale, and the same reference numbers in different figures can denote the same elements. The use of the word about, approximately or substantially means that a value of an element has a parameter that is expected to be close to a stated value or position. However, as is well known in the art there are always minor variances that prevent the values or positions from being exactly as stated. Additionally, descriptions and details of well-known steps and elements may be omitted for simplicity of the description.

DETAILED DESCRIPTION OF THE DRAWINGS

The aspects of the present invention and methods for achieving the aspects will be apparent by referring to the embodiments to be described herein with reference to the accompanying drawings. It is understood that the embodiments described herein are illustrative only and that the present invention is not limited thereto, but can be implemented in alternative forms. Also, it is understood that the features of the various embodiments described herein can be combined with each other, unless specifically noted otherwise.

In general, the present embodiments relate to a microfluidic sensor mounted to a substrate, such as a micro lead frame. The microfluidic sensor is encapsulated or covered with a molding compound resin to provide a package body configured to protect at least portions of the microfluidic sensor from detrimental conditions, such as external forces. In some embodiments, one or more channels are formed in, molded into, formed as part of, or patterned directly into the package body. In other embodiments, one or more mask portions can be placed within molded openings in the package body. In accordance with the present embodiments, the molded channels and/or chambers and/or mask(s) are configured to facilitate the exposure of one or more surfaces of the microfluidic sensor to a material by transporting the material through the channels (dynamic exposure) or by containing the material in the chambers (static exposure). The present embodiments provide, among other things, a microfluidic sensor structure with improved sensor protection and stability, and a more reliable configuration for analyzing materials compared to related devices.

Figures 1, 1A:
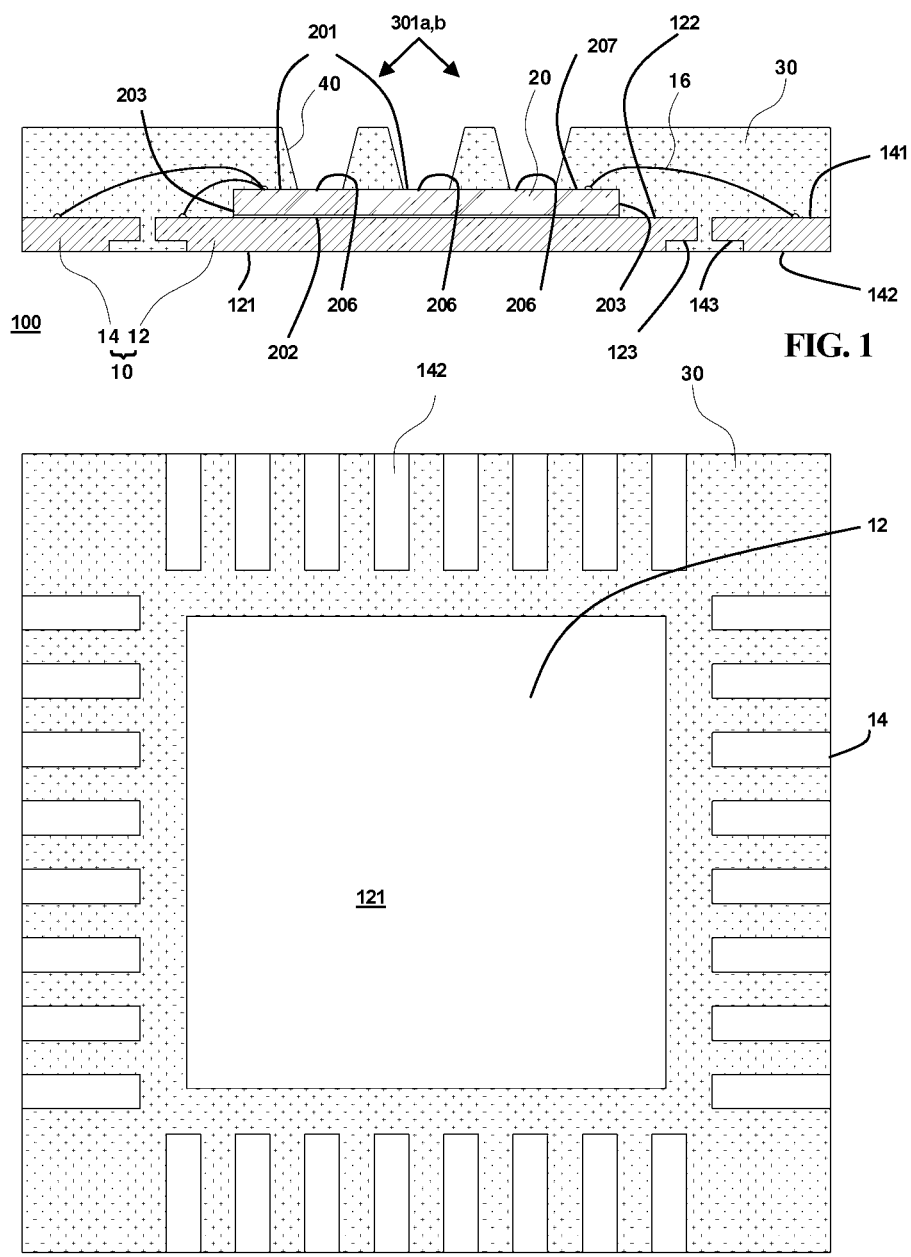
FIG. 1 illustrates a cross-sectional view of a microfluidic sensor device according to a first embodiment of the present invention.
FIG. 1A illustrates a bottom plan view of the embodiment of FIG. 1.
Figure 3A:
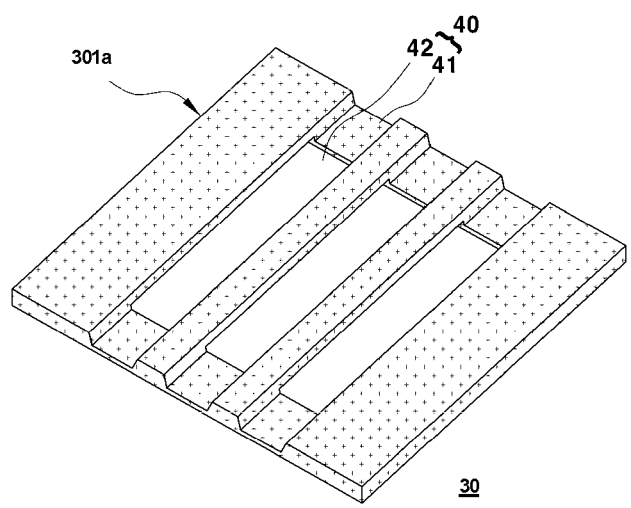
FIGS. 3A and 3B are perspective views illustrating molded package bodies of the microfluidic sensor devices according to the first and second embodiments of the present invention.
Figure 3B:
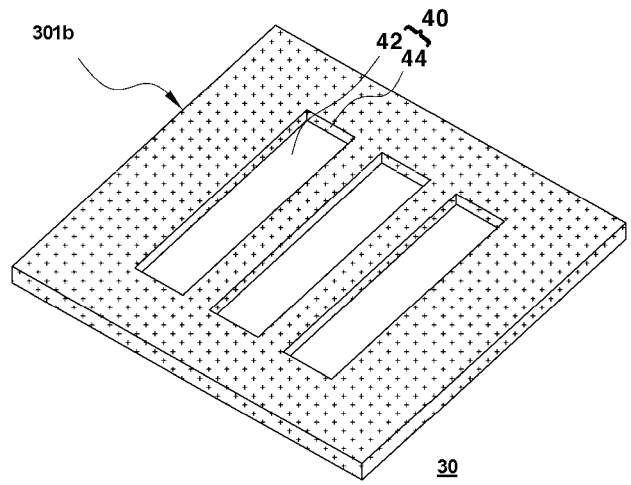

Hereinafter, a microfluidic chip package 100, microfluidic sensor device 100 or microfluidic sensor package 100 according to a first embodiment will be described with reference to FIGS. 1, 1A, 3A, and 3B. FIG. 1 illustrates an enlarged cross-sectional view of microfluidic sensor device 100; FIG. 1A illustrates a bottom plan view of microfluidic sensor device 100; and FIGS. 3A and 3B illustrate partial perspective views of alternative embodiments of a molded package body 30 for use with, for example, microfluidic package 100.

With reference to FIG. 1, microfluidic sensor device 100 includes a substrate 10, which in this embodiment is configured as a micro lead frame (MLF) 10. Micro lead frame 10 is preferred in this embodiment in order to reduce manufacturing costs. Manufacturing costs can be reduced because, for example, MLF style packages can be bulk assembled in a matrix of multiple lead frames and subsequently encapsulated in an overmolding process. The individual MLF structures are then separated into individual packages typically using a singulation process, which separates through the mold compound and the lead frames.

In the present embodiment, micro lead frame 10 includes a chip-mounting plate 12, which includes a bottom or lower surface 121 exposed to the outside through package body 30, and an opposing top surface 122 for receiving a microfluidic sensor 20 or microfluidic chip 20. In one embodiment, chip-mounting plate 12 is provided with a recessed portion or shelf 123 extending inward from lower surface 121 toward top surface 122. In one embodiment, recessed portion 123 can extend laterally around the outer edge portions of chip-mounting plate 12. Micro lead frame 10 further includes a plurality of leads 14 spaced apart from and arranged in a spaced relationship to chip-mounting plate 12 as generally illustrated in FIG. 1A. In one embodiment, leads 14 are on all sides of chip-mounting plate 12. In other embodiments, leads 14 are on fewer than all sides of chip-mounting plate 12. Each lead 14 includes a bonding surface 141 for electrically connecting to microfluidic sensor 20 and an opposing lower surface 142 for mounting to a next level of assembly, such as a printed circuit board. In one embodiment, lower surfaces 142 of leads 14 can be substantially co-planar or flush with lower surface 121 of chip-mounting plate 12. In one embodiment, leads 14 are provided with one or more recessed portions or shelves 143 extending inward from lower surfaces 142 as generally illustrated in FIG. 1.

Micro lead frame 10 typically is made of a conductive material, such as copper or a copper alloy, such as a dual gauge copper alloy. All or portions of micro lead frame 10 can be plated with a conductive material, such as tin (Sn), and/or nickel, palladium, gold, and silver (NiPdAuAg). The features of micro lead frame 10 as described herein can be formed using masking and etching techniques. Alternatively, stamping techniques can be used as well or other techniques as known to those of ordinary skill in the art. In some embodiments, the pitch between leads 14 can be between about 0.25 mm and about 0.85 mm, and the full thickness (i.e., a thickness of the unetched or unrecessed portion of the respective lead) of leads 14 can be between about 0.15 mm and about 0.25 mm.

In one embodiment when film assist molding techniques are used to manufacture microfluidic sensor device 100, an adhesive film (not shown) can be reversibly attached to the entire bottom surface (i.e., surfaces 121 and 142) of micro lead frame 10.

Microfluidic sensor 20 can be attached to the upper surface of chip-mounting plate 12 using, for example, an adhesive such as an epoxy resin. The epoxy resin can be electrically conductive, non-electrically conductive, and/or thermally conductive. As described above, microfluidic sensor 20 can be used in various scientific research fields including, but not limited to DNA analysis, blood analysis, tissue analysis, chemical material and/or reaction studies, biological material studies, disease diagnosis, and/or cell culture analysis. Microfluidic sensor 20 includes a top or first surface 201 configured with a sensor active area 206 for analyzing a material under test and a bonding area or a bonding surface 207 for connecting microfluidic sensor 20 to micro lead frame 10 using, for example, conductive wires 16. In one embodiment, bonding surface 207 includes a plurality of bonding pads (not illustrated) for attaching ends of conductive wires 16 and for receiving and sending electrical signals from microfluidic sensor 20. Microfluidic sensor 20 also includes an opposing bottom or second surface 202 attached to chip-mounting plate 12. Microfluidic sensor 20 further includes side surfaces 203 connect top surface 201 and bottom surface 202.

In one embodiment, after microfluidic sensor 20 is attached to chip-mounting plate 12, conductive wires 16 can be connected to the bonding pads on microfluidic sensor 20 and top surfaces 141 of leads 14 or top surface 122 of chip-mounting plate 12. In one embodiment, one end of each conductive wire 16 can be primarily bonded (referred to as "ball bonding") to a selected bonding pad on microfluidic sensor 20, and the opposing end of the conductive wire 16 is secondarily bonded (referred to as "stitch bonding") to selected top surfaces 141 of leads 14. In some embodiments, one of conductive wires 16 can be ground-bonded to the chip-mounting plate 12 as generally illustrated in FIG. 1.

Subsequently, package body 30 is formed on at least portions of microfluidic sensor 20 and micro lead frame 10. In one embodiment, a film assist molding process can be used to seal or encapsulate microfluidic sensor 20 with a dielectric material, such as an electronic molding compound, encapsulant, or other dielectric material, while an adhesive film is attached to the lower surfaces (for example, lower surfaces 121 and 142) of micro lead frame 10. In accordance with the present embodiment, package body 30 is provided with a patterned or molded panel portion 301a,b having one or more spaces 40 configured for containing a material to be analyzed. Stated another way, molded panel portion 301a,b is an integrated part of package body 30 to provide a single unit package body. In accordance with the present embodiment, spaces 40 in molded panel portion 301a,b are exposed to portions of active area 206 to facilitate contact between microfluidic sensor 20 and a material to be analyzed. Patterned or molded panel portion 301a,b is different than related devices where expensive photolithographic techniques are used to form stand-offs in wafer form before the sensor devices are tested and separated into individual devices. In the present embodiment, molded panel portion 301a,b is formed during the molding process at the same time package body 30 is formed, which saves costs. Also, molded panel portion 301a,b is formed on a known good microfluidic sensor device instead of in wafer form where the stand-off structures are formed on untested devices that could be defective. This further saves manufacturing costs.

FIG. 3A illustrates a partial perspective view of package body 30 having molded panel portion 301*a* or molding compound resin panel 301*a* in accordance with one embodiment, which is formed with a plurality of open channels or tunnels 41 (for example, open at the opposing ends). In this embodiment, open channels 41 can be configured to allow a material being analyzed to flow or pass through open channels 41 and over active surface 206 of microfluidic sensor 20. In accordance with one embodiment, space 40 for containing a material to be analyzed is composed of a plurality of open channels 41 penetrating or extending through the molded panel portion 301*a* to a predetermined depth in one direction, and each of the open channels 41 is provided at the bottom thereof with a reaction hole or opening 42 for exposing active surfaces 206 of the microfluidic sensor 20 to the external or testing environment.

FIG. 3B illustrates a partial perspective view of package body 30 having molded panel portion 301*b* or molding compound resin panel 301*b* in accordance with another embodiment, which is formed with a plurality of sealed channels 44. In accordance with the present embodiment, space 40 for containing a material to be analyzed is composed of a plurality of sealed channels 44 (for example, sealed or closed at opposing ends) penetrating or extending through the molded panel portion 301*b* to a predetermined depth and arranged in parallel with each other in one direction, and each of the sealed channels 44 is provided at the bottom thereof with a reaction hole 42 for exposing active surfaces 206 of the microfluidic sensor 20 to the external or testing environment.

As described above, according to the first embodiment, when microfluidic sensor 20 is sealed with package body 30 having molded panel portion 301*a,b*, microfluidic sensor 20 is better protected from external force. The material to be analyzed is then introduced or charged in space 40 for containing this material, that is, the open channels 41 or the sealed channels 44, which allows the material to make contact with the microfluidic sensor 20. Thus, the analysis of this material using the microfluidic sensor 20 can be more easily performed. In a preferred embodiment, sidewall portions of molded panel portions 301*a,b* in space 40 can be inclined as generally illustrated in FIG. 1. In accordance with the present embodiments, package body 30 and molded panel portion 301*a,b* are formed during a molding process as a single integrated configuration as illustrated in FIGS. 1, 2, 3A and 3B. In one preferred embodiment, package body 30 and molded panel portions 301*a,b* are made of the same material.

Figure 2:
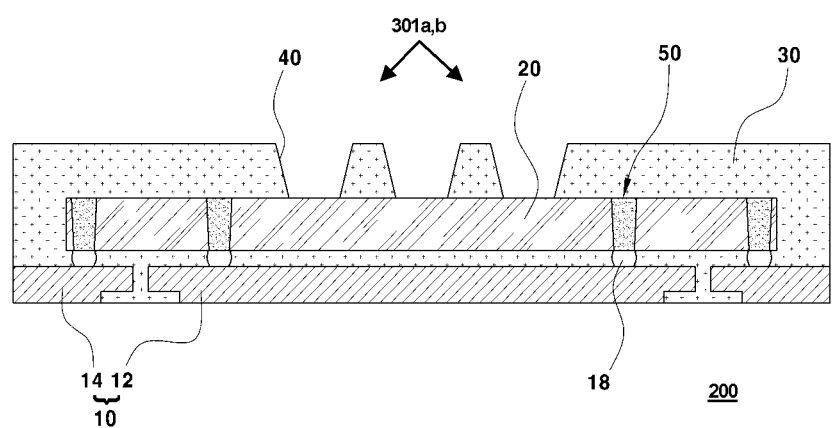
FIG. 2 illustrates a cross-sectional view of a microfluidic sensor device according to a second embodiment of the present invention.

Hereinafter, a microfluidic chip package 200, a microfluidic sensor device 200 or microfluidic sensor package 200 according to a second embodiment will be described with reference to FIGS. 2, 3A, and 3B. Microfluidic sensor device 200 or microfluidic sensor package 200 is substantially similar to microfluidic sensor device 100 of FIGS. 1, 1A, 3A, and 3B and only the significant differences are discussed below.

In microfluidic sensor device 200 according to the second embodiment, microfluidic sensor 20 is connected with each lead 14 of micro lead frame 10 using through-substrate vias 50 and conductive bumps 18 to facilitate receiving and transmitting electrical signals to and from microfluidic sensor 20. By way of example, through-substrate vias 50 can be formed by forming a via having a predetermined depth around the bonding pad of microfluidic sensor 20 and then placing a conductive material in the via. In one embodiment, a bonding pad on microfluidic sensor 20 can be electrically connected or electro-conductively connected with the conductive material of the through-substrate via 50 by a rewiring line (not shown). Bottom surfaces of through-substrate vias 50 can be connected to each lead 14 of micro lead frame 10 using, for example, conductive bumps 18 and a reflow process.

Subsequently, package body 30 is formed on at least portions of microfluidic sensor 20 and micro lead frame 10. In one embodiment, a film assist molding process can be used to seal or encapsulate microfluidic sensor 20 with a dielectric material, such as an electronic molding compound, encapsulant, or other dielectric material, while an adhesive film is attached to the lower surfaces of micro lead frame 10 in the same manner as in the first embodiment. This provides package body 30 with patterned or molded panel portion 301*a,b*. Molded panel portion 301*a,b* is formed having one or more spaces 40 configured for containing a material to be analyzed. In accordance with the present embodiment, spaces 40 (i.e., open channels 41 or the sealed channels 44) in molded panel portion 301*a,b* are formed in or integrated within the molding panel portion 301*a,b* of package body 30. In a preferred embodiment, sidewall portions of molded panel portions 301*a,b* in space 40 can be inclined as generally illustrates in FIG. 2. In accordance with the present embodiments, package body 30 and molded panel portion 301*a,b* are formed during a molding process as a single integrated configuration as illustrated in FIGS. 1, 2, 3A and 3B. In one preferred embodiment, package body 30 and molded panel portions 301*a,b* are made of the same material.

Figure 4:
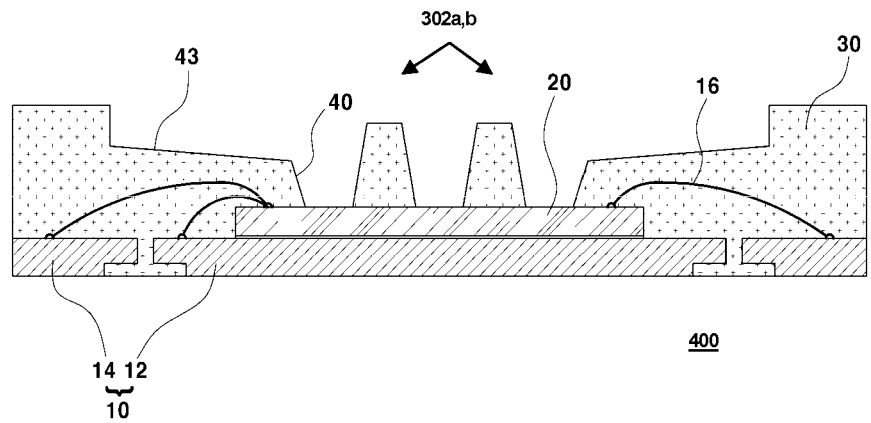
FIG. 4 illustrates a cross-sectional view of a microfluidic sensor device according to a third embodiment of the present invention.

Thus, according to the second embodiment, when microfluidic sensor 20 is sealed with package body 30 having molded panel portion 301*a,b*, microfluidic sensor 20 is better protected from external force. The material to be analyzed is then introduced or charged in space 40 for containing this material, that is, open channels 41 or sealed channels 44, to allow the material to make contact with the microfluidic sensor 20. Thus, the analysis of this material using the microfluidic sensor 20 can be more easily performed Hereinafter, a microfluidic chip packages 400 and 500, microfluidic sensor devices 400 and 500 or microfluidic sensor packages 400 and 500 according to third and fourth embodiments will be described with reference to FIGS. 4 through 6B. As illustrated in FIGS. 4, 6A and 6B, microfluidic sensor device 400 according to the third embodiment is substantially similar to microfluidic sensor 100 of FIGS. 1, 1A, 3A and 3B, and only the significant differences are discussed below. In microfluidic sensor device 400, space 40 for containing a material to be analyzed, which is formed in package body 30, is configured to reduce the overflow of the material to be analyzed.

Figure 5:
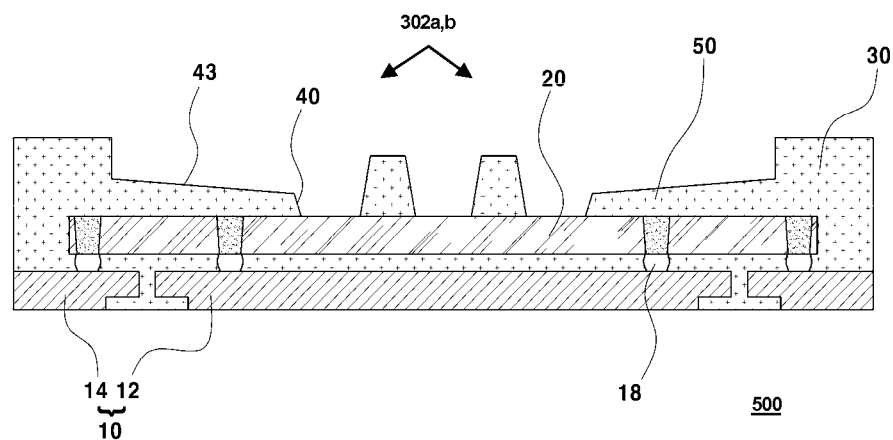
FIG. 5 illustrates a cross-sectional view of a microfluidic sensor device according to a fourth embodiment of the present invention.
Figure 6A:
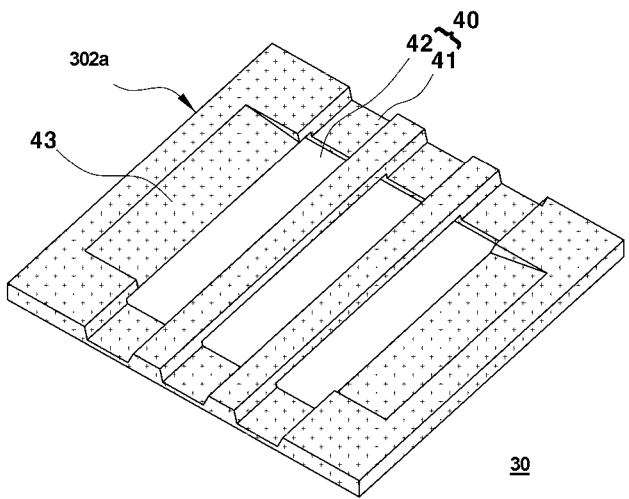
FIGS. 6A and 6B are perspective views illustrating molded package bodies of the microfluidic sensor devices according to the third and fourth embodiments of the present invention.
Figure 6B:
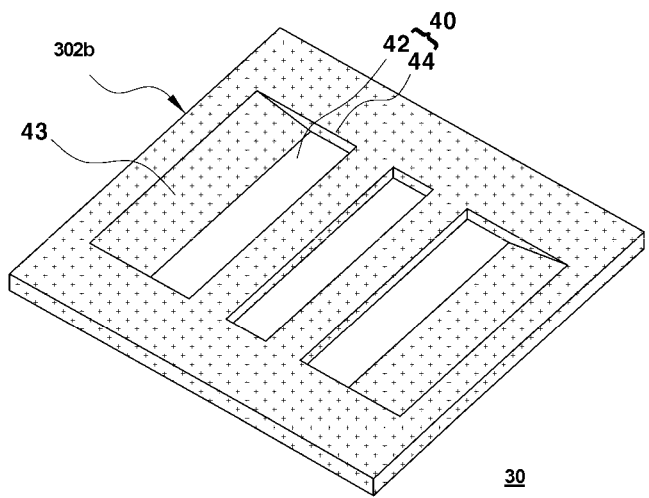
Figure 7:
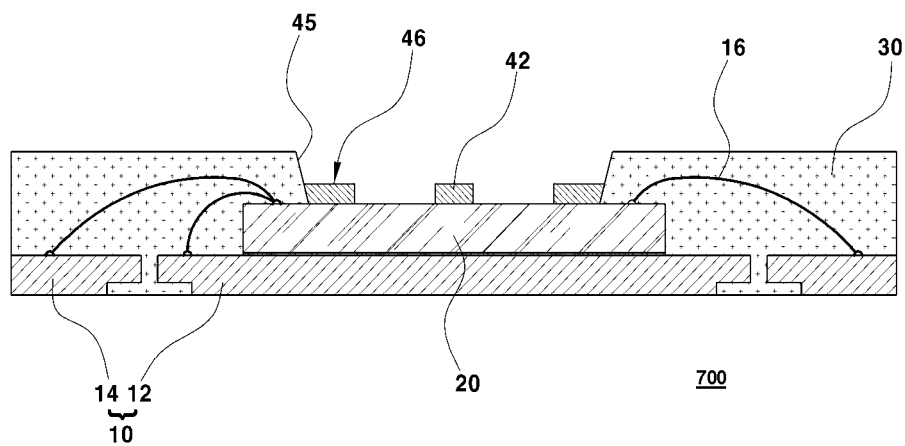
FIG. 7 illustrates a cross-sectional view of a microfluidic sensor device according to a fifth embodiment of the present invention.
Figure 8:
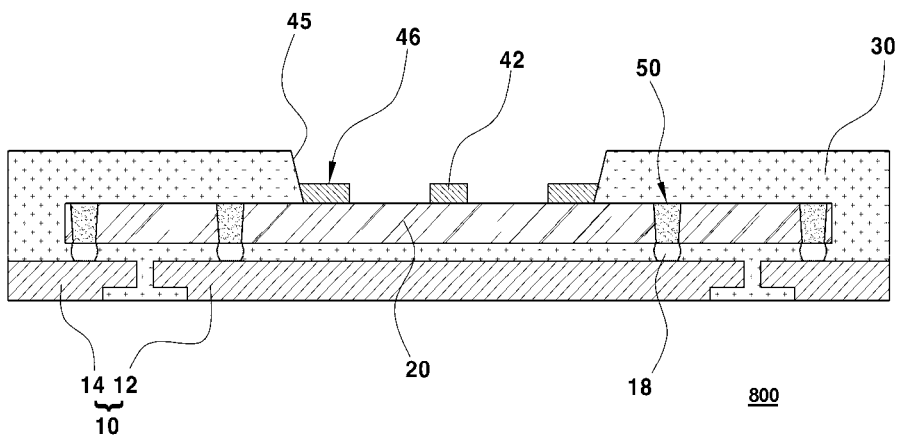
FIG. 8 illustrates a cross-sectional view of a microfluidic sensor device according to a sixth embodiment of the present invention.

As illustrated in FIGS. 5, 6A, and 6B, microfluidic sensor device 500 according to the fourth embodiment is substantially similar to microfluidic sensor device 200 of FIGS. 2 and 3A and 3B, and only the significant differences are discussed below. In microfluidic sensor device 500, the space 40 for containing a material to be analyzed, which is formed in package body 30, is configured to prevent the overflow of the material to be analyzed.

As illustrated in FIG. 6A, space 40 for containing a material to be analyzed according to the third and fourth embodiments includes a plurality of open channels 41 formed in molded panel portion 302*a* or molding compound resin panel 302*a* to a predetermined depth in one direction, and each of the open channels 41 is provided at the bottom thereof with a reaction hole 42 for exposing active surfaces 206 of the microfluidic sensor 20 to the external or testing environment. In the accordance with this embodiment, space 40 further includes a structure configured to at least partially contain excess material during testing. In one embodiment space 40 includes an inclined multi-stage chamber 43 (e.g., a two-stage chamber) for preventing the overflow of the material being analyzed. In one embodiment, inclined multi-stage chamber 43 can be formed in the upper portion of the molded resin panel 302a of package body 30 adjacent to the outermost open channels 41.

Further, as illustrated in FIG. 6B, space 40 for containing a material to be analyzed according to the third and fourth embodiments includes a plurality of sealed channels 44 formed in the molded panel portion 302b or molding compound resin panel 302b to a predetermined depth and arranged in parallel with each other in one direction, and each of the sealed channels 44 is provided at the bottom thereof with a reaction hole 42 for exposing the surface of the microfluidic sensor 20 to the external or testing environment. In accordance with this embodiment, space 40 includes inclined multi-stage chamber 43 for preventing the overflow of material being analyzed. In one embodiment, inclined multi-stage chamber 43 can be formed in the upper portion of the molded resin panel 302b of package body 30 adjacent to the outermost chambers 44.

Therefore, even when the material to be analyzed is injected into the open channels 41 or the sealed channels 44 in a predetermined amount or more, the inclined multi-stage chamber 43 is configured to contain or retain any excess amount of the material to be analyzed, thus reducing the likelihood that material overflows outside of microfluidic sensor devices 400 and 500. In a preferred embodiment, sidewall portions of molded panel portions 302a,b in space 40 can be inclined as generally illustrated in FIGS. 4 and 5. In accordance with the present embodiments, package body 30 and molded panel portion 302a,b are formed during a molding process as a single integrated configuration as illustrated in FIGS. 4, 5, 6A and 6B. In one preferred embodiment, package body 30 and molded panel portions 302a,b are made of the same material.

Hereinafter, a microfluidic chip packages 700 and 800, microfluidic sensor devices 700 and 800 or microfluidic sensor packages 700 and 800 according to fifth and sixth embodiments will be described with reference to FIGS. 7 through 9C. As illustrated in FIGS. 7, 9A, 9B and 9C, microfluidic sensor device 700 according to the fifth embodiment is substantially similar to microfluidic sensor device 100 of FIG. 1, and only the significant differences are discussed below. In microfluidic sensor device 700, space 40 for containing a material to be analyzed is formed in package body 30 and is further defined by patterned panel portion(s), patterned mask(s), patterned insert(s), mask(s), or insert(s) 46.

Further, as illustrated in FIGS. 8, 9A, 9B, and 9C, microfluidic sensor device 800 according to the sixth embodiment is substantially similar to microfluidic sensor device 200 of FIG. 2, and only the significant differences are discussed below. In microfluidic sensor device 800, space 40 for containing a material to be analyzed is defined by patterned panel portion(s), patterned mask(s), patterned insert(s), mask(s), or insert(s) 46. In some embodiments, mask 46 and package body 30 comprise different materials.

As illustrated in FIGS. 7 through 9C, the space 40 for containing a material to be analyzed according to the fifth and sixth embodiments is constructed such that mask 46, which has a plurality of reaction holes 42, is attached to the surface of the microfluidic sensor 20 within space or opening 45 formed in the upper surface of package body 30. Opening 45 is configured to facilitate the exposure of microfluidic sensor 20 to the external or testing environment.

Figure 9A:
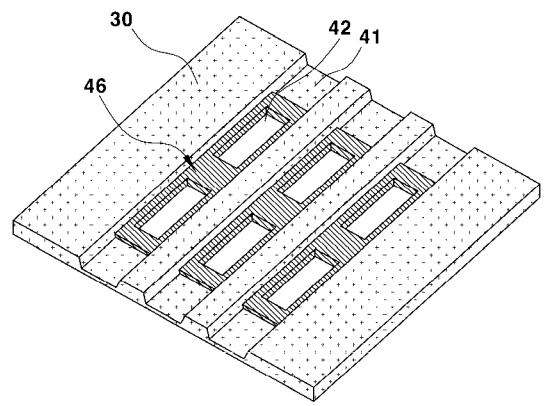
FIGS. 9A, 9B and 9C are perspective views illustrating molded package bodies having mask portions of the microfluidic sensor devices according to the fifth and sixth embodiments of the present invention.
Figure 9B:
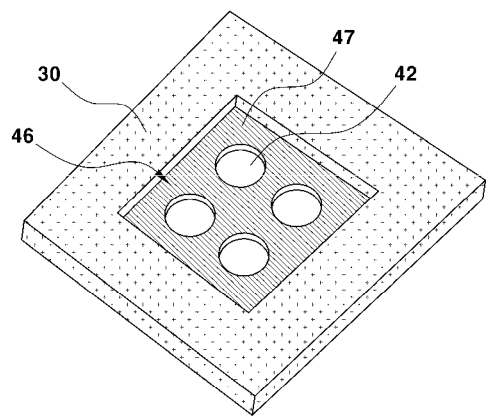
Figure 9C:
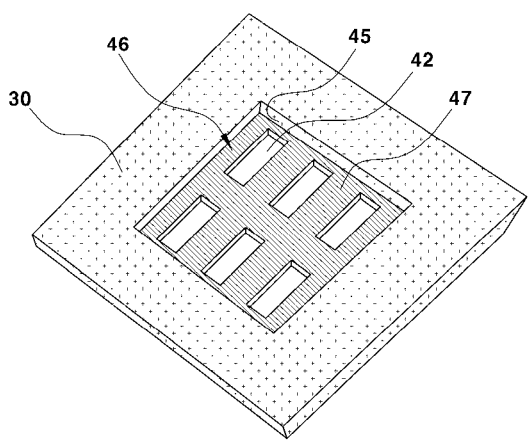

As illustrated in FIG. 9A, package body 30 can be formed with an open channel structure 41, such as molded panel portions 301a or 302a described previously. Masks 46 can then be attached to or formed on microfluidic sensor 20 and/or package body 30 within open channel structure 41. In other embodiments as illustrated in FIGS. 9B and 9C, mask 46 can be attached to microfluidic sensor 30 and/or package body 30 within an open channel structure 41, sealed channels 44, or a sealed chamber structure 47. In accordance with the present embodiments, masks 46 are provided with reaction holes 42 for exposing active surfaces 206 of microfluidic sensor 20.

In accordance with one embodiment, masks 46 can be a patterned photoresist material, and reaction holes 42 for exposing the surface of the microfluidic sensor 20 can be formed by a general exposure process. In other embodiments, masks 46 can be other materials subsequently patterned using, for example, photolithographic processes. In some embodiments, masks 46 can be separately formed inserts. In some embodiments, masks 46 are recessed within opening 45 below the upper surface of package body 30.

Thus, in accordance with the fifth and sixth embodiments, when microfluidic sensor 20 is sealed with package body 30, the microfluidic sensor 20 is better protected from external force. The material to be analyzed is then introduced or charged in the space for containing this material (for example: reaction holes 42 in the mask(s) 46) to allow the material to make contact with the microfluidic sensor 20, and thus the analysis of this material using the microfluidic sensor 20 can be more easily performed.

From all of the foregoing, one skilled in the art can determine that according to one embodiment, a microfluidic sensor device (for example, elements 100, 200, 400, 500, 700, 800) comprises a micro lead frame (for example, element 10) including a chip-mounting plate (for example, element 12) and a plurality of leads (for example, element 14) arranged around the chip-mounting plate in multiple directions such that they are flush with the chip-mounting plate; a microfluidic sensor (for example, element 20) is disposed on the chip-mounting plate of the micro lead frame; a conductive connector (for example, elements 16, 18, 50) electrically connecting or electro-conductively connecting the microfluidic sensor and each of the leads; and a molded package body (for example, element 30) disposed on the entire upper surface of the micro lead frame to cover the microfluidic sensor and molded with a space (for example, element 40) for containing a material to be analyzed to expose a part of the upper surface of the microfluidic sensor.

Those skilled in the art will appreciate that according to another embodiment, a microfluidic sensor device (for example, elements 100, 200, 400, 500, 700, 800) comprises microfluidic sensor (for example, element 20) mounted on and electrically connected to a micro lead frame (for example, element 10). The microfluidic sensor is molded with a molding compound resin to form a package body (for example, element 30) that protects the microfluidic sensor from external force. The package body includes a molded panel portion (for example, element 301a, 301b, 302a, 302b) and, in some embodiments, a mask portion (for example, element 46) having a channel(s) (for example, element 41, 44) or chamber (for example, element 44, 45) for exposing an active surface (for example, element 206) of the microfluidic sensor to allow a material to be analyzed to flow through the channel or to be contained in the chamber.

Those skilled in the art will also appreciate that according to a further embodiment, a microfluidic sensor device (for example, elements 100, 200, 400, 500, 700, 800) comprises a micro lead frame (for example, element 10) including a chip-mounting plate (for example, element 12) and a plurality of leads (for example, element 14) arranged around the chip-mounting plate in all directions such that they are flush with the chip-mounting plate; a microfluidic sensor (for example, element 20) is disposed on the chip-mounting plate of the micro lead frame; a conductive connector (for example, element 16, 18, 50) electrically connects the microfluidic sensor and at least some of the leads; and package body (for example element 30) having a molding compound resin panel (for example, element 301a, 301b, 302a, 302b) is disposed on the entire upper surface of the micro lead frame to cover the microfluidic sensor and is provided with a space (for example, element 40, 45) for containing a material to be analyzed and to expose a part of the upper surface of the microfluidic sensor to analyze the material.

In another embodiment, the space (for example, element 40) for containing a material to be analyzed may include a plurality of open channels (for example, element 41) penetrated and formed in the package body (for example, element 30) to a predetermined depth in one direction, and each of the open channels may be provided at a bottom thereof with a reaction hole (for example, element 42) for exposing the surface of the microfluidic sensor to the outside.

In a further embodiment, an inclined multi-stage chamber (for example, element 43) for preventing the overflow of the material to be analyzed may be further formed in an upper portion of package body. In another embodiment, the inclined multi-stage chamber can be adjacent to an outermost channel or chamber.

In another embodiment, the space (for example, element 40) for containing a material to be analyzed may include a plurality of sealed channels (for example, element 44) formed in the package body to a predetermined depth and arranged in parallel with each other in one direction, and each of the sealed channels may be provided at a bottom thereof with a reaction hole (for example, element 42) for exposing the surface (for example, element 206) of the microfluidic sensor to the outside.

In a further embodiment, an inclined multi-stage chamber (for example, element 43) for containing the overflow of the material to be analyzed may be further formed in an upper portion of the package body. In another embodiment, the multi-stage chamber can be adjacent to an outermost channel or chamber.

In a still further embodiment, the space (for example, element 40, 45) for containing a material to be analyzed may be configured such that a mask (for example, element 46) having a plurality of reaction holes (for example, element 42) is attached to the surface of the microfluidic sensor in a state in which a single opening for exposing the microfluidic sensor to the outside is formed in an upper surface of the package body. In one embodiment, the mask is formed in the opening after the package body is formed.

In another embodiment, the mask may be provided on the surface thereof with any one selected from an open channel, a sealed channel, and a sealed chamber, and each of the open channel, the sealed channel, and the sealed chamber may be provided at the bottom thereof with a reaction hole for exposing the surface of the microfluidic sensor.

In yet another embodiment, the conductive connectors electrically connecting the microfluidic sensor to the substrate (e.g., micro lead frame) may be a conductive wire (for example, element 16) connecting the microfluidic sensor with each of the leads or a conductive bump (for example, element 18) connecting a through-substrate via (for example, element 50) formed in the microfluidic sensor with each of the leads.

Those skilled in the art will also appreciate that according to another embodiment, a microfluidic sensor device (for example, elements 100, 200, 400, 500, 700, 800) comprises a substrate (for example, element 10) comprising a chip-mounting plate (for example, element 12) and a plurality of leads (for example, element 14) spaced apart from and arranged in spaced relationship to the chip-mounting plate. A microfluidic sensor (for example, element 20) having an active surface (for example, element 206) and a bonding surface (for example, element 207), wherein the microfluidic sensor is coupled to the chip-mounting portion and electrically coupled to the leads. A package body (for example, element 30) encapsulates at least portions of the substrate and the microfluidic chip, wherein the package body comprises a molded panel portion (for example, element 301a, 301b, 302a, 302b) defining a space (for example, element 40, 45) that exposes at least portion of the active surface of the microfluidic sensor.

In another embodiment, the molded panel portion can comprise a plurality of open channels (for example, element 41) extending through the molded panel portion to a predetermined depth in one direction, wherein each of the open channels is provided with a reaction hole (for example, element 42) for exposing the active surfaces the microfluidic sensor to a testing environment. In a further embodiment, the molded panel portion comprises a plurality of sealed channels (for example, element 44) extending through the molded panel portion to a predetermined depth and arranged in parallel with each other in one direction, wherein each of the sealed channels is provided with a reaction hole (for example, element 42) for exposing the active surface of the microfluidic sensor to a testing environment. In a still further embodiment, the molded panel portion can comprise a sealed chamber (for example, element 45). In another embodiment, the package body can further comprise a structure (for example, element 43) configured to contain excess material during testing. In a further embodiment, the package body and the molded panel portion comprises a single integrated configuration. In a still further embodiment, at least portions of the space can comprise inclined sidewalls. In yet another embodiment, the device can further comprise a mask portion (for example, element 46) adjoining the active surface of the microfluidic sensor within the space, wherein the mask portion comprises a plurality reaction holes (for example, element 42) extending to the active surface. In another embodiment, the substrate can comprise a micro lead frame, and the microfluidic sensor further comprises a plurality of through-substrate vias (for example, element 50) electrically coupled to the leads.

Those skilled in the art will also appreciate that according to another embodiment a method for forming a microfluidic sensor device comprises providing a substrate (for example, element 10) comprising a chip-mounting plate (for example, element 12) and a plurality of leads (for example, element 14) spaced apart and arranged in spaced relationship to the chip-mounting plate. The method includes attaching a microfluidic sensor (for example, element 20) to the chip-mounting portion, wherein microfluidic sensor has an active surface (for example, element 206), and wherein the microfluidic sensor is electrically coupled (for example, elements 16, 18, 50) to the leads. The method includes forming a package body (for example, element 30) encapsulating at least portions of the substrate and the microfluidic chip, wherein the package body comprises a molded panel portion (for example, element 301*a*, 301*b*, 302*a*, 302*b*) defining a space (for example, element 40, 45) that exposes at least a portion of the active surface of the microfluidic sensor.

In another embodiment, forming the package body can comprise forming the package body and the molded panel portion as a single integrated structure where the package body and the molded panel portion comprise the same material. In a further embodiment, forming the package body can comprise forming the molded panel portion having one or more of a plurality of open channels (for example, element 41), a plurality of sealed channels (for example, element 44), and a sealed chamber (for example, element 45). In a still further embodiment, forming the package body can comprise forming a structure (for example, element 43) configured to contain excess material during testing. In another embodiment, the method can further comprise placing a mask structure (for example, element 46) in the space after forming the package body.

Those skilled in the art will also appreciate that according to other embodiments, the mask structure (for example, element 46) can be recessed within the space (for example, elements 40, 45); the lower surfaces of leads (for example, element 142) and/or the chip-mounting plate (for example, element 121) can be exposed in the package body; the leads and/or the chip-mounting portion can include recessed portions (for example, element 123, 143); the bonding surface (for example, element 207) of the microfluidic sensor can be encapsulated by the package body; the mask portion can be a prefabricated insert structure; the containment structure (for example, element 43) can be configured to drain away excess material from the space; or/and a separate lid or cap structure can be attached to the molded resin panel or mask structure.

In view of all the above, it is evident that a novel structure and method is disclosed. Included in one embodiment, among other features, a microfluidic sensor is molded with a molding compound resin to protect the microfluidic sensor from external force, and an open channel, sealed channel, or sealed chamber for exposing the active surface(s) of the microfluidic sensor is provided in a molded panel portion of the package body and/or a mask, which are configured to allow a material to be analyzed to flow through the open channel(s) or to be contained in the sealed channels or chamber therein. Thus, the material to be analyzed can be more easily analyzed by the microfluidic sensor. Additionally, the microfluidic sensor is sealed with a molding compound resin to enhance protection of the microfluidic sensor from external force. Further, in some embodiments, the substrate for mounting the microfluidic sensor includes a reduced cost micro lead frame substrate. Finally, the microfluidic sensor device has improved sensor protection and stability, and a more reliable configuration for analyzing materials compared to related devices.

While the subject matter of the invention is described with specific preferred embodiments and example embodiments, the foregoing drawings and descriptions thereof depict only typical embodiments of the subject matter, and are not therefore to be considered limiting of its scope. It is evident that many alternatives and variations will be apparent to those skilled in the art. For example, the configurations of molded panel portions 301*a*, 301*b*, 302*a*, and 302*b* and the configurations of masks 46 are illustrative only and other patterns, shapes, and configurations are possible for providing desired spaces to test or analyze materials. Additionally, masks 46 can be a separately formed insert attached to microfluidic sensor 20 and/or package body 30 using, for example, an adhesive material before or after package body 30 is formed. For example, mask 46 can be attached after microfluidic sensor 20 is attached to the substrate, such as micro lead frame 10. Film assist molding techniques can be used to form space 40 or chamber 45.

Also, package body 30 can be formed by overmolding and saw-through techniques, formed by cavity molding and punch techniques, or formed by other techniques as known to those of ordinary skill in the art.

As the claims hereinafter reflect, inventive aspects may lie in fewer than all features of a single foregoing disclosed embodiment. Thus, the hereinafter expressed claims are hereby expressly incorporated into this Detailed Description of the Drawings, with each claim standing on its own as a separate embodiment of the invention. Furthermore, while some embodiments described herein include some but not other features included in other embodiments, combinations of features of different embodiments are meant to be within the scope of the invention, and form different embodiments, as would be understood by those skilled in the art.

We claim:

1. A microfluidic sensor device comprising:
   a substrate comprising a chip-mounting plate and a plurality of leads spaced apart from and arranged in spaced relationship to the chip-mounting plate, wherein the chip-mounting plate and the plurality of leads comprise a conductive material, and wherein the chip-mounting plate has a chip-mounting plate top surface and a chip-mounting plate lower surface opposite to the chip-mounting top surface, and wherein each of the plurality of leads has a top lead surface and a lower lead surface opposite to the top lead surface;
   a microfluidic sensor having an active surface and a bonding surface opposite to the active surface, wherein the bonding surface is coupled to the chip-mounting plate top surface and electrically coupled to the leads; and
   a package body encapsulating at least portions of the substrate and the microfluidic chip, wherein the package body comprises a molded panel portion adjacent the active surface and defining a space that exposes at least portion of the active surface of the microfluidic sensor, and wherein the chip-mounting plate lower surface and the lower lead surface of each of the plurality of leads are exposed to the outside through a bottom surface of the package body.

2. The device of claim 1, wherein the molded panel portion comprises a plurality of open channels extending through the molded panel portion to a predetermined depth in one direction, wherein each of the open channels is provided with a reaction hole for exposing the active surfaces the microfluidic sensor to a testing environment.

3. The device of claim 1, wherein the molded panel portion comprises a plurality of sealed channels extending through the molded panel portion to a predetermined depth and arranged in parallel with each other in one direction, wherein each of the sealed channels is provided with a reaction hole for exposing the active surface of the microfluidic sensor to a testing environment.

4. The device of claim 1, wherein the molded panel portion comprises a sealed chamber.

5. The device of claim 1, wherein the package body further comprises a structure configured to contain excess material during testing.

6. The device of claim wherein the package body and the molded panel portion comprise a single integrated configuration such that the molded panel portion is an integrated part of the package body to provide a single unit package body.

7. The device of claim 1, wherein at least portions of the space comprise inclined sidewalls.

8. The device of claim 1 further comprising a mask portion adjoining the active surface of the microfluidic sensor within the space, wherein the mask portion comprises a plurality reaction holes extending to the active surface.

9. The device of claim 8, wherein:
the substrate comprises a micro lead frame; and
the microfluidic sensor further comprises a plurality of through-substrate vias electrically coupled to the leads.

10. A method for forming a microfluidic sensor device comprising:
providing a substrate comprising a chip-mounting plate and a plurality of leads spaced apart from and arranged in spaced relationship to the chip-mounting plate, wherein the chip-mounting plate and the plurality of leads comprise a conductive material, and wherein the chip-mounting plate has a chip-mounting plate top surface and a chip-mounting plate bottom surface opposite to the chip-mounting top surface, and wherein each of the plurality of leads has a top lead surface and a bottom lead surface opposite to the top lead surface;
attaching a bonding surface of a microfluidic sensor to the chip-mounting plate top surface, wherein microfluidic sensor has an active surface opposite to the bonding surface, and wherein the microfluidic sensor is electrically coupled to the leads; and
forming a package body encapsulating at least portions of the substrate and at least portions of the microfluidic chip, wherein the package body comprises a molded panel portion disposed adjacent the active surface and defining a space that exposes at least portion of the active surface of the microfluidic sensor, and wherein a chip-mounting plate bottom surface and the lead surface of each of the plurality of leads are exposed to the outside through a bottom surface of the package body.

11. The method of claim 10, wherein forming the package body comprises:
forming the package body and the molded panel portion as a single integrated structure where the package body and the molded panel portion comprises the same material;
forming the molded panel portion having one or more of a plurality of open channels, a plurality of sealed channels, and a sealed chamber; and
forming a structure configured to contain excess material during testing.

12. The method of claim 10 further comprising placing a mask structure in the space after forming the package body, wherein forming the package body comprises forming the package body and the molded panel portion comprising a single integrated configuration such that the molded panel portion is an integrated part of the package body to provide a single unit package body.

* * * * *